US009939380B2

(12) United States Patent
Wang et al.

(10) Patent No.: US 9,939,380 B2
(45) Date of Patent: Apr. 10, 2018

(54) DETECTION DEVICE AND METHOD FOR SIMULTANEOUS IN-SITU MEASUREMENT OF DISSOLVED OXYGEN AT DIFFERENT SUBMERGED PLANT LEAF-WATER INTERFACE LEVELS

(71) Applicants: Nanjing Institute of Environmental Sciences, Ministry of Environmental Protection, P. R. C., Nanjing, Jiangsu Province (CN); Chongqing University of Arts and Sciences, Chongqing (CN)

(72) Inventors: Wenlin Wang, Nanjing (CN); Weixin Li, Nanjing (CN); Qiang Li, Chongqing (CN); Bo Liu, Nantong (CN); Yinjing Wan, Nanjing (CN); Ruiming Han, Nanjing (CN); Xiaoyan Tang, Nanjing (CN); Wenjing Li, Nanjing (CN); Fei He, Nanjing (CN); Wei Zhuang, Nanjing (CN); Changxin Zou, Nanjing (CN); Aiping Liu, Nanjing (CN); Shoujing Yin, Beijing (CN); Xiaohan Li, Beijing (CN); Guoquan Pan, Nanjing (CN); Weimin Wang, Nanjing (CN)

(73) Assignees: Nanjing Institute of Environmental Sciences, Ministry of Environmental Protection, P.R.C., Nanjing (CN); Chongqing University of Arts and Sciences, Chongqing (CN)

( * ) Notice: Subject to any disclaimer, the term of this patent is extended or adjusted under 35 U.S.C. 154(b) by 0 days.

(21) Appl. No.: 15/331,035

(22) Filed: Oct. 21, 2016

(65) Prior Publication Data
US 2017/0219490 A1    Aug. 3, 2017

(30) Foreign Application Priority Data
Feb. 3, 2016    (CN) .......................... 2016 1 0076049

(51) Int. Cl.
*G01N 21/00* (2006.01)
*G01N 21/64* (2006.01)

(52) U.S. Cl.
CPC ......... *G01N 21/645* (2013.01); *G01N 21/643* (2013.01); *G01N 2021/6432* (2013.01); *G01N 2021/6484* (2013.01)

(58) Field of Classification Search
CPC ............. G01N 21/6428; G01N 21/643; G01N 21/645; G01N 2021/6432; G01N 2021/6484

(58) Field of Classification Search
USPC ............................................ 250/221, 227.11
See application file for complete search history.

(56) References Cited

U.S. PATENT DOCUMENTS

| 2013/0046164 A1* | 2/2013 | Liu ..................... A61B 5/14503 600/364 |
| 2017/0219491 A1* | 8/2017 | Li ........................ G01N 21/636 |

* cited by examiner

*Primary Examiner* — Kevin Pyo
(74) *Attorney, Agent, or Firm* — Hauptman Ham, LLP (57) ABSTRACT

A detection device for simultaneous in-situ measurement of dissolved oxygen at different submerged plant leaf-water interface levels. The detection device includes a dissolved oxygen micro-optrode host. A plurality of detection probes are externally connected to the dissolved oxygen micro-optrode host and can extend out probes. The detection device includes a leaf clamp having an upper clamping head, a lower clamping head, a hinged shaft and a clamping handle. Each of the upper and lower clamping head includes a plurality of water passing cavities penetrating through the back and the front thereof. Each of the upper and lower clamping head includes a plurality of slots horizontally extending inwardly of the corresponding clamping head. The detection device includes a plurality of insertion pieces having a probe groove. The detection probe is locatable in the respective probe groove for fixation. The insertion pieces are insertable and fixable in the slots.

10 Claims, 8 Drawing Sheets

DETECTION DEVICE AND METHOD FOR SIMULTANEOUS IN-SITU MEASUREMENT OF DISSOLVED OXYGEN AT DIFFERENT SUBMERGED PLANT LEAF-WATER INTERFACE LEVELS

TECHNICAL FIELD

The invention relates to the technical field of dissolved oxygen detection device, and in particular to a detection device and method for simultaneous in-situ measurement of dissolved oxygen at different submerged plant leaf-water interface levels.

BACKGROUND ART

Dissolved oxygen micro-optrode belongs to the technology of one-dimensional microprobes for implementing measurement of a dissolved oxygen concentration at a certain point of submerged plant leaves. It is an optical fiber information exchange sensor based on the fluorescence quenching principle. As oxygen is the natural quenching agent for some fluorescent indicators, an oxygen-sensitive fluorescent indicator is made into an oxygen sensing film that is then coupled with an end portion of an optical fiber. High-brightness light-emitting diodes are adopted as a light source and a miniature photodiode test system. Then, oxygen concentrations can be determined according to optical fiber conducted florescence quenching intensities. Ruthenium complexes are applied most extensively so far because of their characteristics of insensitivity to stirring, inactivity to interferences of $H_2S$, $CO_2$ and salinity, and the like.

The existing method for detecting dissolved oxygen at the submerged plant leaf-water interface using the dissolved oxygen micro-optrode is to put submerged plant leaves to be tested in a test container first, then retain a dissolved oxygen detection probe to the top of the container, control a fluorescent probe on the dissolved oxygen detection probe to extend downwards until being positioned around the submerged plant leaves, and emit laser to the probe by the dissolved oxygen micro-optrode, thereby measuring the dissolved oxygen in water at the end portion of the probe under the fluorescence quenching principle.

The method has the following defects:

1. It fails in realizing in-situ measurement, and requires a submerged plant leaf sample for putting into the test container, which may easily cause a change to the natural environment around the submerged plant leaves, leading to inconsistency of the dissolved oxygen condition of the sampled submerged plant leaves with the actual condition.

2. Only one dissolved oxygen micro-optrode could be controlled each time to detect the dissolved oxygen condition at a certain level in a certain position of the submerged plant leaves, and for the submerged plant leaves, the dissolved oxygen conditions at other levels in the position can be obtained only through multiple measurement which, however, has a large span in time and fails in reflecting the actual conditions.

3. Single measurement can only be performed on one side of the submerged plant leaves, and the dissolved oxygen conditions on both front and back sides of the submerged plant leaves cannot be measured simultaneously.

SUMMARY

The technical problem to be solved by the present invention is to provide a detection device and method for simultaneous in-situ measurement of dissolved oxygen at different submerged plant leaf-water interface levels in view of the above technical present situation.

A detection device for simultaneous in-situ measurement of dissolved oxygen at different submerged plant leaf-water interface levels comprises a dissolved oxygen micro-optrode host, wherein a plurality of detection probes are externally connected to the dissolved oxygen micro-optrode host and can extend out probes used for detecting dissolved oxygen, wherein the detection device further comprises a leaf clamp, and the leaf clamp consists of an upper clamping head, a lower clamping head, a hinged shaft and a clamping handle; submerged plant leaves are clamped between the upper clamping head and the lower clamping head, and each of the upper clamping head and the lower clamping head is provided with a plurality of water passing cavities penetrating through the back and the front thereof, and each of the upper clamping head and the lower clamping head is further provided with a plurality of slots horizontally extending inwardly of the corresponding clamping head; the slots are communicated with each water passing cavity; and the detection device further comprises a plurality of insertion pieces, each of the insertion pieces is provided with a probe groove, the detection probe can be placed in the respective probe groove for fixation, and the insertion pieces can be inserted and fixed in the slots, and the probes extending out can be positioned in different water passing cavities by adjusting the depths of the insertion pieces into the slots.

In order to optimize the above technical solution, an additional specific measure is adopted as follows:

The openings of the slots are positioned at the front end surfaces of the upper clamping head and the lower clamping head.

The upper clamping head, the lower clamping head and the clamping handle can all rotate around the hinged shaft, and opening and closing of the upper clamping head and the lower clamping head are controlled by pressing the clamping handle around the hinged shat.

The detection probe comprises a flexible optical fiber and a rigid optical fiber, wherein the rigid optical fiber is the probe and the rear end of the rigid optical fiber is connected to the dissolved oxygen micro-optrode host through the flexible optical fiber.

The detection probe further comprises a probe pushing structure, wherein the probe pushing structure comprises a pushing pipe, a pushing column, a friction block, a seal ring, a pushing handle and a pipe backseat; the pushing handle is connected to the rear end of the pushing column, the front end of the pushing column is extended into the pushing pipe to be fixedly connected to the friction block in the pushing pipe, the friction block is frictionally engaged with the inner wall of the pushing pipe, the pipe backseat blocks off the rear end of the pushing pipe, the friction block is fixedly connected to the rear part of the probe, the seal ring is fixed in the pushing pipe, to seal and divide a cavity of the pushing pipe into a front cavity and a rear cavity, the front cavity is provided with a through window through which water can enter the front cavity, and accordingly, each probe groove is provided with a groove window at a position corresponding to the through window, so that the through window is communicated with the water passing cavity when the insertion piece fixing the detection probe is fixed in the slot; and when an external force for propelling the pushing handle is larger than a friction between the friction block and the pushing pipe, the friction block slides in the pushing pipe, so that the probe extends out into the front cavity.

The flexible optical fiber is fixedly connected to the pushing handle.

A plurality of fixing grooves are formed in the side of the insertion piece; a fixing boss is arranged in the slot; and when the insertion piece is inserted into the slot, the fixing grooves are clamped into the fixing boss, so that the insertion piece is in stationary fit with a detection kit, and the depth of the insertion piece inserted into the slot is adjusted by selecting different fixing grooves to be clamped with the fixing boss.

A detection method for simultaneous in-situ measurement of dissolved oxygen at different submerged plant leaf-water interface levels comprises the following steps:

Step 1, assembling a detection device, namely selecting a plurality of detection probes as required, specifying slots, clamping each detection probe into a probe groove of a corresponding insertion piece to ensure that the detection probe and the insertion piece are positioned, and then inserting the insertion pieces into the specified slots;

Step 2, pushing out a probe of each detection probe into a front cavity of a pushing pipe;

Step 3, extending a leaf clamp into water, clamping submerged plant leaves between an upper clamping head and a lower clamping head, wherein front and back leaf surfaces of the submerged plant leaves respectively are communicated with the water passing cavity on the upper clamping head and/or lower clamping head, and injecting water into the water passing cavity and the front cavity of the pushing pipe;

Step 4, collecting dissolved oxygen data in the water by each probe, transmitting the data to a dissolved oxygen micro-optrode host, and displaying after analyzing and processing the data by the dissolved oxygen micro-optrode host.

When all the insertion pieces are inserted into the slots on the upper or lower clamping head, the detection device will detect the dissolved oxygen at one side of the submerged plant leaf; when the insertion pieces are inserted into the upper and lower clamping heads, the detection device will detect the dissolved oxygen at both the front and back sides of the submerged plant leaf.

Step 5, after detection is completed, lifting the leaf clamp from the water body, and taking out the insertion pieces, wherein the method of taking out the insertion pieces comprises: pulling a pushing handle backwards, so that the friction block slides backwards; when the friction block slides to the rear end of the pushing pipe, enabling the probes to be retracted to the rear cavity of the pushing pipe; continuously pulling the pushing handle backwards; the friction block abuts against the pipe backseat, so that the whole insertion piece moves backwards; and the fixing grooves exit from the fixing boss to draw out the insertion piece.

Compared with the prior art, the detection device and the detection method thereof have the following advantages:

1. The submerged plant leaf is clamped by the leaf clamps for detection, so that the leaf may be prevented from moving and thus from influencing the detected results.

2. The present invention comprises a plurality of detection probes which operate at the same time, so that a plurality of detection probes may simultaneously detect the dissolved oxygen of the front and back sides of the submerged plant leaf at the leaf-water interface at different heights, which avoids repeated detections in multiple times, saves the time and obtains the real distribution of the dissolved oxygen amount at the front and back sides of the submerged plant leaf at different heights at the same time.

3. When the present invention is used for measuring the dissolved oxygen of the submerged plant at the leaf-water interface, a sample of the submerged plant leaf need not be taken into a detection container, but rather, the leaf clamps for clamping the leaves are directly immersed in the water where the submerged plant leaf to be detected is positioned, which avoids changes in the natural environment around the submerged plant leaf and achieves the in-site detection completely.

4. The detection on the dissolved oxygen at the submerged plant leaf surfaces at different heights may be finished in one time, which is very convenient.

The reference numerals are as follows: dissolved oxygen micro-optrode host 1, detection probe 2, probe 21, flexible optical fiber 22, leaf clamp 3, upper clamping head 31, lower clamping head 32, hinged shaft 33, clamping handle 34, water passing cavity 35, slot 36, fixing boss 37, insertion piece 4, probe groove 41, groove window 41$a$, fixing groove 42, probe pushing structure 5, pushing pipe 51, front cavity 51$a$, rear cavity 51$b$, pushing column 52, friction block 53, seal ring 54, pushing handle 55, pipe backseat 56, through window 57, submerged plant leaf 6.

DETAILED DESCRIPTION OF THE INVENTION

Embodiments of the present invention will be described in further details with reference to the accompanying drawings.

As shown in FIGS. 1 to 9, the detection device for simultaneous in-situ measurement of dissolved oxygen at different submerged plant leaf-water interface levels of the present invention comprises a dissolved oxygen micro-optrode host 1, and a plurality of detection probes 2 are connected to the dissolved oxygen micro-optrode host 1 and can extend out probes 21 used for detecting dissolved oxygen, wherein the detection device further comprises a leaf clamp 3, and the leaf clamp 3 consists of an upper clamping head 31, a lower clamping head 32, a hinged shaft 33 and a clamping handle 34; submerged plant leaves are clamped between the upper clamping head 31 and the lower clamping head 32, each of the upper clamping head 31 and the lower clamping head 32 is provided with a plurality of water passing cavities 35 penetrating through the back and the front thereof, and each of the upper clamping head 31 and the lower clamping head 32 is further provided with a plurality of slots 36 horizontally extending inwardly of the corresponding clamping head; the slots 36 are communicated with each water passing cavity 35; and the detection device further comprises a plurality of insertion pieces 4, wherein each of the insertion pieces 4 is provided with a probe groove 41, the detection probes 2 can be placed in the respective probe grooves 41 for fixation, and the insertion pieces 4 can be inserted and fixed in the slots 36, and the probes 21 extending out can be positioned in different water passing cavities 35 by adjusting the depths of the insertion pieces 4 into the slots 36.

Figure 1:
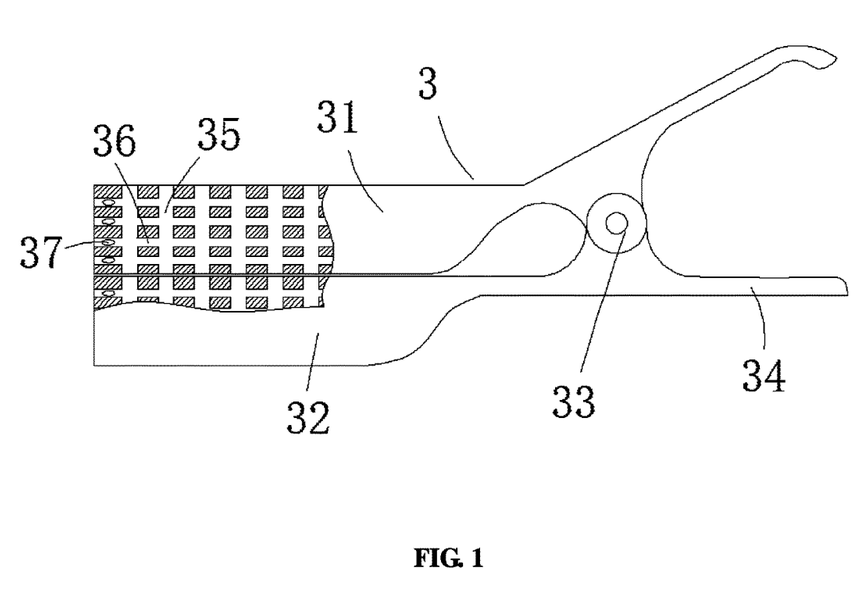
FIG. 1 is a structural schematic view of a leaf clamp.
Figure 2:
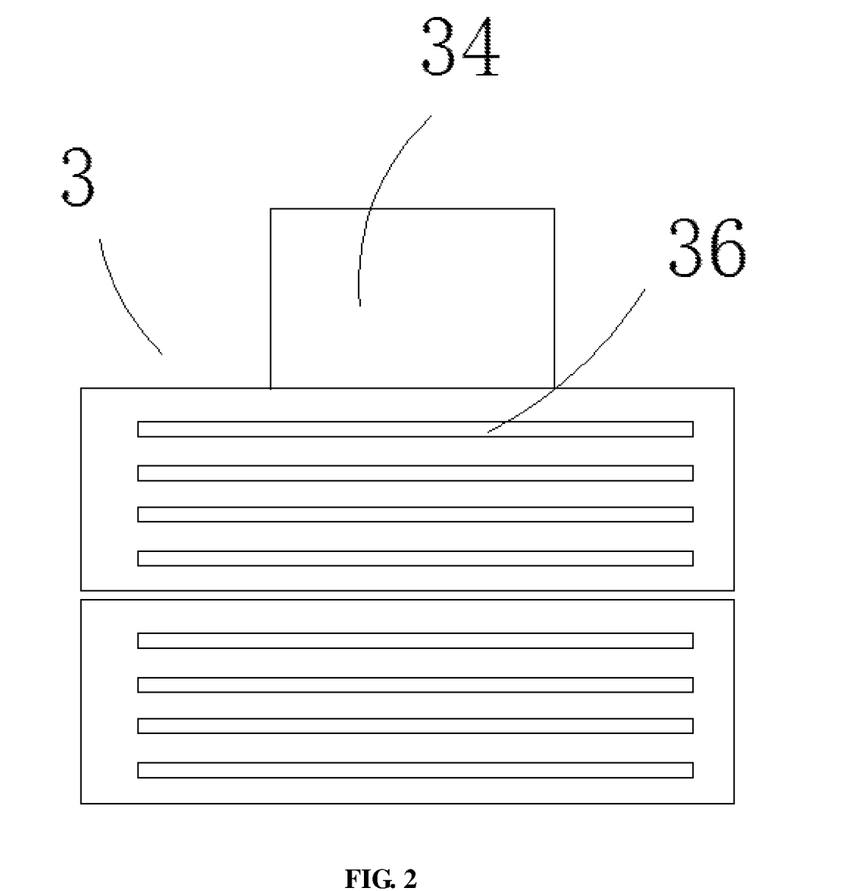
FIG. 2 is a left view of FIG. 1.

In the embodiments, the openings of the slots 36 are positioned at the front end surfaces of the upper clamping head 31 and the lower clamping head 32.

In the embodiment, the upper clamping head 31, the lower clamping head 32 and the clamping handle 34 can all rotate around the hinged shaft 33, and opening and closing of the upper clamping head 31 and the lower clamping head 32 are controlled by pressing the clamping handle 34 around the hinged shaft 33.

Figure 3:
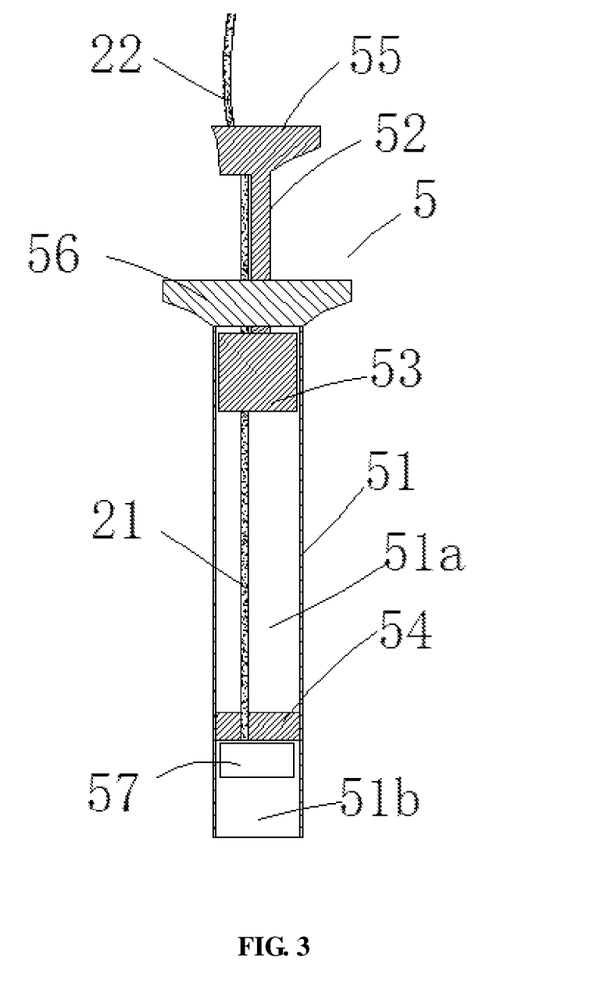
FIG. 3 is a structural schematic view of a detection probe.

In the embodiment, the detection probe 2 comprises a flexible optical fiber 22 and a rigid optical fiber, wherein the rigid optical fiber is the probe 21 and the rear end of the rigid optical fiber is connected to the dissolved oxygen micro-optrode host 1 through the flexible optical fiber 22.

Figure 5:
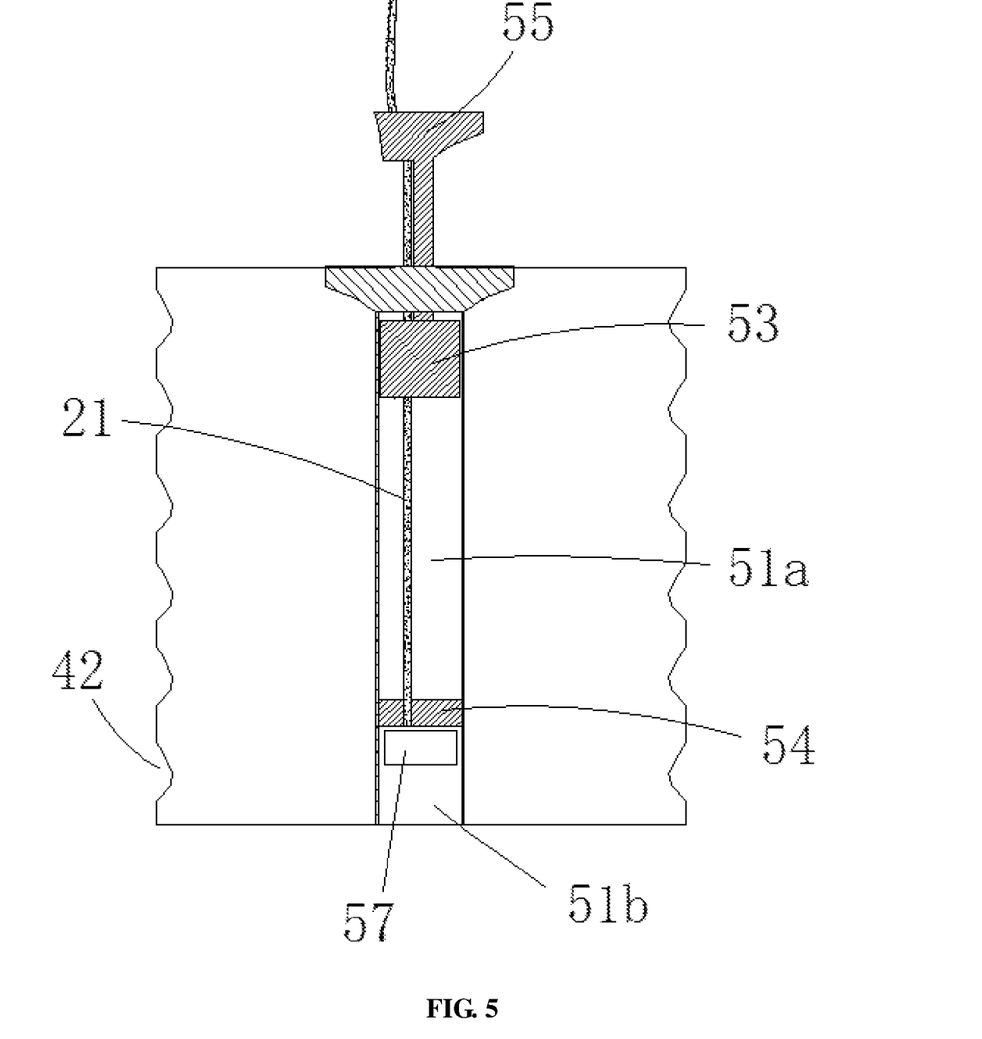
FIG. 5 is a schematic view of a detection probe placed in an insertion piece.
Figure 6:
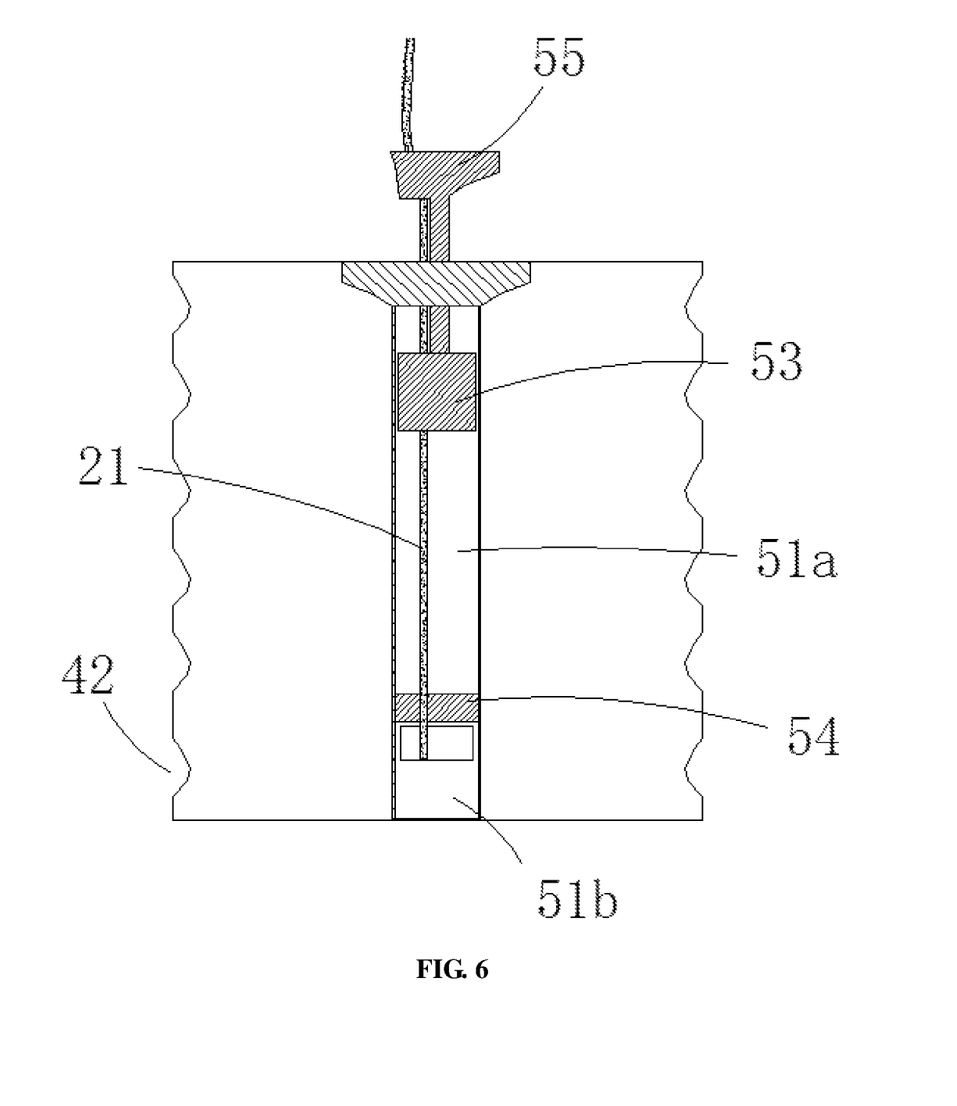
FIG. 6 is a schematic view of a probe extending outwards.

In the embodiment, the detection probe 2 further comprises a probe pushing structure 5, wherein the probe pushing structure 5 comprises a pushing pipe 51, a pushing column 52, a friction block 53, a seal ring 54, a pushing handle 55 and a pipe backseat 56; the pushing handle 55 is connected to the rear end of the pushing column 52, the front end of the pushing column 52 is extended into the pushing pipe 51 to be fixedly connected to the friction block 53 in the pushing pipe 51, the friction block 53 is frictionally engaged with the inner wall of the pushing pipe 51, the pipe backseat 56 blocks off the rear end of the pushing pipe 51; the friction block 53 is fixedly connected to the rear part of the probe 21, the seal ring 54 is fixed in the pushing pipe 51 to seal and divide a cavity of the pushing pipe 51 into a front cavity 51a and a rear cavity 51b, the front cavity 51a is provided with a through window 57, through which water can enter the front cavity 51a, and accordingly, the probe groove 41 is provided with a groove window 41a at a position corresponding to the through window 57, so that the through window 57 is communicated with the corresponding water passing cavity 35 when the insertion piece 4 fixing the detection probe 2 is fixed in the slot 36; and when an external force for propelling the pushing handle 55 is larger than a friction force between the friction block 53 and the pushing pipe 51, the friction block 53 slides in the pushing pipe 51, so that the probe 21 extends out into the front cavity 51a.

In the embodiment, the flexible optical fiber 22 is fixedly connected to the pushing handle 55.

Figure 4:
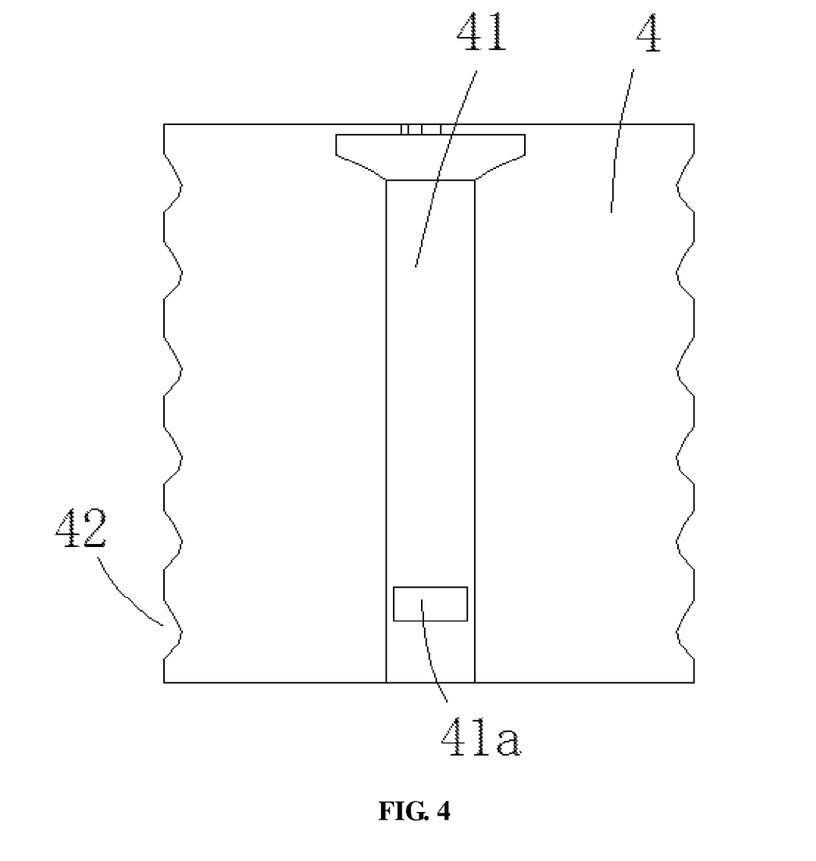
FIG. 4 is a structural schematic view of an insertion piece.
Figure 7:
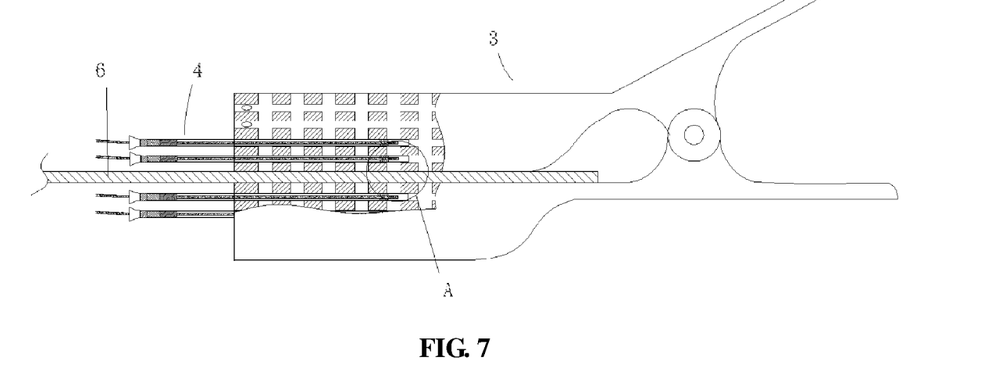
FIG. 7 is a schematic view of an insertion piece inserted into a leaf clamp and detection of dissolved oxygen at the front and back sides of a submerged plant leaf.
Figure 8:
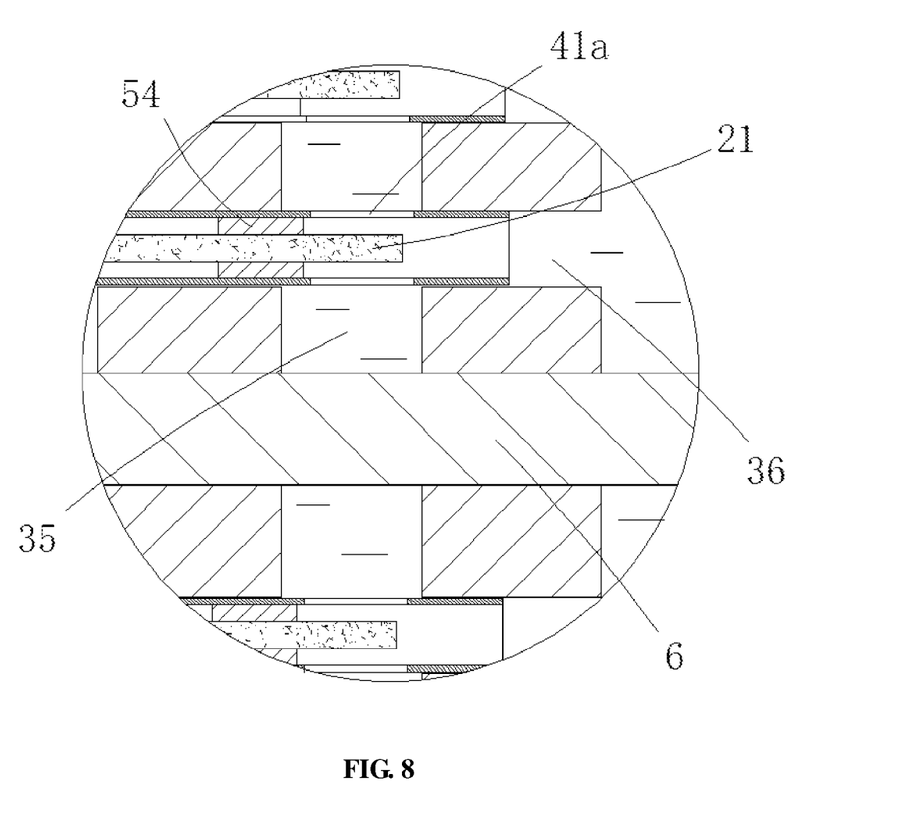
FIG. 8 is an enlarged structural view of part A of FIG. 7.

In the embodiment, a plurality of fixing grooves 42 are formed in the side of the insertion piece 4, a fixing boss 37 is arranged in the slot 36, when the insertion piece 4 is inserted into the slot 36, the fixing grooves 42 are clamped into the fixing boss 37, so that the insertion piece 4 is in stationary fit with a detection kit 3, and the depth of the insertion piece 4 inserted into the slot 36 is adjusted by selecting different fixing grooves 42 to be clamped with the fixing boss 37.

Figure 9:
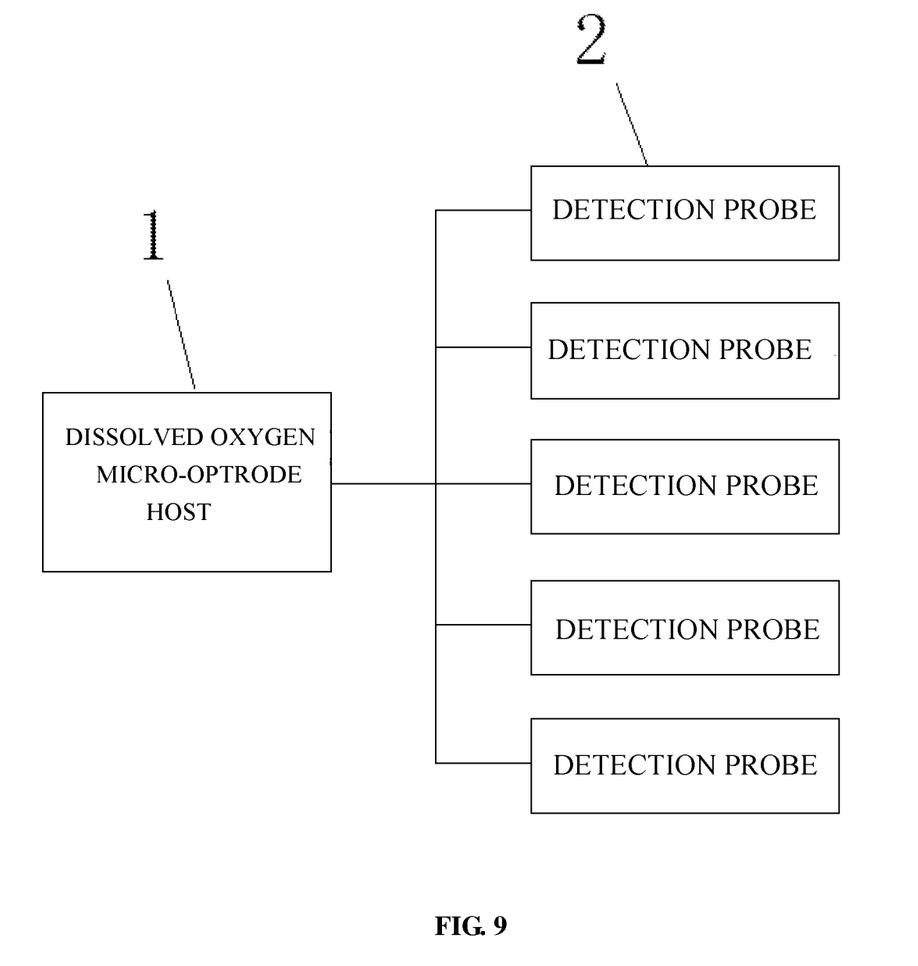
FIG. 9 is a structural schematic block diagram of dissolved oxygen micro-optrode.

A detection method for simultaneous in-situ measurement of dissolved oxygen at different submerged plant leaf-water interface levels comprises the following steps:

Step 1, assembling a detection device, namely selecting a plurality of detection probes 2 as required, specifying slots 36, clamping each detection probe 2 into a probe groove 41 of a corresponding insertion piece 4 to ensure that the detection probe 2 and the insertion piece 4 are positioned, and then inserting the insertion pieces 4 into the specified slots 36;

Step 2, pushing out a probe 21 of each detection probe 2 into a front cavity 51a of a pushing pipe 51;

Step 3, extending a leaf clamp 3 into water, clamping submerged plant leaves between an upper clamping head 31 and a lower clamping head 32, wherein front and back leaf surfaces of the submerged plant leaves respectively are communicated with the water passing cavity 35 on the upper clamping head 31 and/or lower clamping head 32, and injecting water into the water passing cavity 35 and the front cavity 51a of the pushing pipe 51;

Step 4, collecting dissolved oxygen data in the water by each probe 21, transmitting the data to a dissolved oxygen micro-optrode host 1, and displaying after analyzing and processing the data by the dissolved oxygen micro-optrode host 1;

Step 5, after detection is completed, lifting the leaf clamp 3 from the water body, and taking out the insertion pieces 4, wherein the method of taking out the insertion pieces 4 comprises: pulling the pushing handle 55 backwards, so that the friction block 53 slides backwards; when the friction block 53 slides to the rear end of the pushing pipe 51, enabling the probes 21 to be retracted to the rear cavity 51b of the pushing pipe 51, continuously pulling the pushing handle 55 backwards; the friction block 53 abuts against the pipe backseat 56, so that the whole insertion piece 4 moves backwards; and the fixing grooves 42 exit from the fixing boss 37 to draw out the insertion piece 4.

When all the insertion pieces 4 are inserted into the slots 36 on the upper clamping head 31 or lower clamping head 32, the detection device will detect the dissolved oxygen at one side of the submerged plant leaf; when the insertion pieces 4 are inserted into the upper clamping head 31 or lower clamping head 32, the detection device will detect the dissolved oxygen at both the front and back sides of the submerged plant leaf.

According to the present invention, the height of the leaf clamp 3 does not exceed 1 cm, the thickness of the insertion piece 4 is about 1 mm, and 4-8 inserting pieces 4 can be inserted into one leaf clamp 3.

The detection probes 2 adopted by the embodiment are fluorescent probes, and the probes detect the dissolved oxygen of the submerged plant leaves according to the following principle: a dissolved oxygen micro-optrode host 1 is used for emitting lasers, the lasers are emitted to the probes 21 through a flexible optical fiber 22, the front ends of the probes 21 are provided with an oxygen fluorescence sensitive material, the lasers are emitted to the oxygen fluorescence sensitive material, and the fluorescence generated by fluorescence quencher effect is fed back to the dissolved oxygen micro-optrode host 1, the dissolved oxygen micro-optrode host 1 converts the flourescent signal into an electric signal, demodulates the electric signal, and compares the demodulated electric signal with a dissolvable oxygen concentration change relation, so that dissolvable oxygen concentration information is obtained. The oxygen fluorescence sensitive material can be selected from various fluorescent sensitive materials in prior, and good materials are ruthenium complexes, such as $Ru(dpp)_3Cl_2$.

The above are only preferable embodiments of the present invention, the scope of the present invention is not limited to the embodiments, and the technical scheme under the spirit of the present invention belongs to the scope of the present invention. It should be noted that for those of skilled in the art, various modifications and improvements without departing from the principles shall be within the scope of the present invention.

The invention claimed is:

1. A detection device for simultaneous in-situ measurement of dissolved oxygen at different submerged plant leaf-water interface levels, comprising a dissolved oxygen micro-optrode host, wherein a plurality of detection probes are externally connected to the dissolved oxygen micro-optrode host and can extend out probes used for detecting dissolved oxygen, and characterized in that the detection device further comprises a leaf clamp, and the leaf clamp consists of an upper clamping head, a lower clamping head, a hinged shaft and a clamping handle; submerged plant leaves are clamped between the upper clamping head and the lower clamping head, each of the upper clamping head and the lower clamping head is provided with a plurality of water passing cavities penetrating through the back and the front thereof, and each of the upper clamping head and the lower clamping head is further provided with a plurality of slots horizontally extending inwardly of the corresponding clamping head; the slots are communicated with each water passing cavity; and the detection device further comprises a plurality of insertion pieces, wherein each of the insertion pieces is provided with a probe groove, the detection probe can be placed in the respective probe groove for fixation, the insertion pieces can be inserted and fixed in the slots, and the probes extending out can be positioned in different water passing cavities by adjusting the depths of the insertion pieces into the slots.

2. The detection device for simultaneous in-situ measurement of dissolved oxygen at different submerged plant leaf-water interface levels according to claim 1, wherein openings of the slots are positioned at the front end surfaces of the upper clamping head and the lower clamping head.

3. The detection device for simultaneous in-situ measurement of dissolved oxygen at different submerged plant leaf-water interface levels according to claim 2, wherein the upper clamping head, the lower clamping head and the clamping handle can all rotate around the hinged shaft, and opening and closing of the upper clamping head and the lower clamping head are controlled by pressing the clamping handle around the hinged shaft.

4. The detection device for simultaneous in-situ measurement of dissolved oxygen at different submerged plant leaf-water interface levels according to claim 3, wherein the detection probe comprises a flexible optical fiber and a rigid optical fiber, wherein the rigid optical fiber is the probe and the rear end of the rigid optical fiber is connected to the dissolved oxygen micro-optrode host through the flexible optical fiber.

5. The detection device for simultaneous in-situ measurement of dissolved oxygen at different submerged plant leaf-water interface levels according to claim 4, wherein the detection probe further comprises a probe pushing structure, wherein the probe pushing structure comprises a pushing pipe, a pushing column, a friction block, a seal ring, a pushing handle and a pipe backseat; the pushing handle is connected to the rear end of the pushing column, the front end of the pushing column is extended into the pushing pipe to be fixedly connected to the friction block in the pushing pipe, the friction block is frictionally engaged with the inner wall of the pushing pipe, the pipe backseat blocks off the rear end of the pushing pipe, the friction block is fixedly connected to the rear part of the probe, the seal ring is fixed in the pushing pipe to seal and divide a cavity of the pushing pipe into a front cavity and a rear cavity, the front cavity is provided with a through window through which water can enter the front cavity, and accordingly, the probe groove is provided with a groove window at a position corresponding to the through window, so that the through window is communicated with the water passing cavity when the insertion piece fixing the detection probe is fixed in the slot; and when an external force for propelling the pushing handle is larger than a friction force between the friction block and the pushing pipe, the friction block slides in the pushing pipe, so that the probe extends out into the front cavity.

6. The detection device for simultaneous in-situ measurement of dissolved oxygen at different submerged plant leaf-water interface levels according to claim 5, wherein the flexible optical fiber is fixedly connected to the pushing handle.

7. The detection device for simultaneous in-situ measurement of dissolved oxygen at different submerged plant leaf-water interface levels according to claim 6, wherein a plurality of fixing grooves are formed in the side of the insertion piece; a fixing boss is arranged in the slot; and when the insertion piece is inserted into the slot, the fixing grooves are clamped into the fixing boss, so that the insertion piece is in stationary fit with a detection kit, and the depth of the insertion piece inserted into the slot is adjusted by selecting different fixing grooves to be clamped with the fixing boss.

8. A detection method for simultaneous in-situ measurement of dissolved oxygen at different submerged plant leaf-water interface levels, wherein by comprising the following steps:
step 1, assembling a detection device, namely selecting a plurality of detection probes as required, specifying slots, clamping each detection probe into a probe groove of a corresponding insertion piece to ensure that the detection probe and the insertion piece are positioned, and then inserting the insertion pieces into the specified slots;
step 2, pushing out a probe of each detection probe into a front cavity of a pushing pipe;
step 3, extending a leaf clamp into water, clamping submerged plant leaves between an upper clamping head and a lower clamping head, wherein front and back leaf surfaces of the submerged plant leaves respectively are communicated with the water passing cavity on the upper clamping head and/or lower clamping head, and injecting water into the water passing cavity and the front cavity of the pushing pipe;
step 4, collecting dissolved oxygen data in the water by each probe, transmitting the data to a dissolved oxygen micro-optrode host, and displaying after analyzing and processing the data by the dissolved oxygen micro-optrode host.

9. The detection method for simultaneous in-situ measurement of dissolved oxygen at different submerged plant leaf-water interface levels according to claim 8, wherein when all the insertion pieces are inserted into the slots on the upper clamping head or lower clamping head, the detection device will detect the dissolved oxygen at one side of the submerged plant leaf; when the insertion pieces are inserted into the upper clamping head and lower clamping head, the detection device will detect the dissolved oxygen at both the front and back sides of the submerged plant leaf.

10. The detection method for simultaneous in-situ measurement of dissolved oxygen at different submerged plant leaf-water interface levels according to claim 8, wherein by further comprising step 5, namely after detection is completed, lifting the leaf clamp from the water body, and taking out the insertion pieces, wherein the method of taking out the insertion pieces comprises: pulling a pushing handle backwards, so that the friction block slides backwards; when the friction block slides to the rear end of the pushing pipe, the probes are retracted to the rear cavity of the pushing pipe; continuously pulling the pushing handle backwards; the friction block abuts against the pipe backseat, so that the whole insertion piece moves backwards; and the fixing grooves exit from the fixing boss to draw out the insertion piece.

* * * * *